(12) United States Patent
Gerasimenko et al.

(10) Patent No.: US 11,027,128 B2
(45) Date of Patent: Jun. 8, 2021

(54) DEVICE FOR NON-INVASIVE ELECTRICAL STIMULATION OF THE SPINAL CORD

(71) Applicants: COSYMA LTD, Moscow (RU); THE REGENTS OF THE UNIVERSITY OF CALIFORNIA, Oakland, CA (US)

(72) Inventors: Yuri Petrovich Gerasimenko, Leningradskaya obl. (RU); Alexandr Alekseevich Grishin, Moscow (RU); Tatiana Romulievna Moshonkina, Sankt-Peterburg (RU)

(73) Assignees: COSYMA LTD, Moscow (RU); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 154 days.

(21) Appl. No.: 16/067,173

(22) PCT Filed: Nov. 29, 2016

(86) PCT No.: PCT/RU2016/050077
§ 371 (c)(1),
(2) Date: Jun. 29, 2018

(87) PCT Pub. No.: WO2017/116290
PCT Pub. Date: Jul. 6, 2017

(65) Prior Publication Data
US 2019/0022382 A1    Jan. 24, 2019

(30) Foreign Application Priority Data
Dec. 29, 2015    (RU) .......................... RU2015156833

(51) Int. Cl.
*A61N 1/36*    (2006.01)
(52) U.S. Cl.
CPC ..... *A61N 1/36034* (2017.08); *A61N 1/36003* (2013.01)

(58) Field of Classification Search
None
See application file for complete search history.

(56) References Cited

U.S. PATENT DOCUMENTS

| 2009/0204175 A1 | 8/2009 | Zanella et al. | |
| 2013/0083447 A2* | 4/2013 | D'Andrea | H05C 1/00 361/232 |

(Continued)

FOREIGN PATENT DOCUMENTS

| RU | 2 201 729 | 4/2003 |
| RU | 2 204 423 | 5/2003 |

(Continued)

OTHER PUBLICATIONS

International Search Resort issued in Appln. No. PCT/RU2016/050077 dated Apr. 13, 2017.

(Continued)

*Primary Examiner* — Ankit D Tejani
(74) *Attorney, Agent, or Firm* — Nixon & Vanderhye P.C.

(57) ABSTRACT

A device for the noninvasive stimulation of the spinal cord, intended for carrying out diagnostic tests and physiotherapy. A spinal cord electrostimulator includes five stimulation channels with an electrode system, each of the channels includes connected in series a voltage converter, a current generator and an output signal generator and it is configured to be able to generate the following rectangular pulses: rhythmic modulated bipolar, rhythmic modulated monopolar, rhythmic non-modulated monopolar, single non-modulated monopolar. The inputs of each of the channels are coupled to a microcontroller, which is connected to an indication unit, a control unit and a radio module. The microcontroller is configured to trigger at least one said channel, to select a triggering mode independently for each of the channels, to control each of said channels with (Continued)

parameters of the pulses and vary said parameters depending on a degree of damage to a spinal segment.

7 Claims, 12 Drawing Sheets

(56) References Cited

U.S. PATENT DOCUMENTS

| | | | |
|---|---|---|---|
| 2014/0180361 A1 | 6/2014 | Burdick et al. | |
| 2014/0336727 A1* | 11/2014 | Perryman | A61N 1/36146 |
| | | | 607/59 |
| 2015/0148868 A1* | 5/2015 | Shahandeh | A61N 1/37217 |
| | | | 607/60 |

FOREIGN PATENT DOCUMENTS

| | | |
|---|---|---|
| RU | 2 471 518 | 1/2013 |
| RU | 2 529 471 | 9/2014 |
| RU | 2 545 440 | 3/2015 |
| WO | WO 2013/071307 | 5/2013 |
| WO | WO 2015/048563 | 4/2015 |

OTHER PUBLICATIONS

Written Opinion of the International Searching Authority issued in Appln. No. PCT/RU2016/050077 dated Apr. 13, 2017.
Courtine et al., "Transformation of nonfunctional spinal circuits into functional states after the loss of brain input" *Nat Neurosci.* Oct. 2009; 12(10): 1333-1342. doi:10.1038/nn.2401.
Dimitrijevic et al., "Evidence for a Spinal Central Pattern Generator in Humans" Ann. N.Y. Acad. Sci., Nov. 16, 1998, 860: p. 360-376.
Gerasimenko et al., "Formation of Locomotor Patterns in Decerebrate Cats in Conditions of Epidural Stimulation of the Spinal Cord" *Neuroscience and Behavioral Physiology*, vol. 35, No. 3, 2005, 291-298.
Harkema et al., "Effect of Epidural stimulation of the lumbosacral spinal cord on voluntary movement, standing, and assisted stepping after motor complete paraplegia: a case study" *Lancet*, Jun. 4, 2011; 377(9781): 1938-1947. doi:10.1016/S0140-6736(11)60547-3.
Ichiyama et al., "Hindlimb stepping movements in complete spinal rats induced by epidural spinal cord stimulation" *Neuroscience Letters*, 383 (2005) 339-344.
Krenn et al., "Selectivity of transcutaneous stimulation of lumbar posterior roots at different spinal levels in humans" *Biomed Tech*, 2013; 58 (Suppl. 1).

\* cited by examiner

| Unmodulated pulse | | | | | |
|---|---|---|---|---|---|
| 10Hz | | 30Hz | | 99 Hz | |
| Set current (mA) | Measured current (mA) | Set current (mA) | Measured current (mA) | Set current (mA) | Measured current (mA) |
| 0 | 1 | 0 | 0 | 0 | 1 |
| 5 | 8 | 5 | 7 | 5 | 5 |
| 6 | 9 | 6 | 8 | 6 | 8 |
| 7 | 9 | 7 | 9 | 7 | 7 |
| 8 | 10 | 8 | 10 | 8 | 9 |
| 9 | 8 | 9 | 8 | 9 | 11 |
| 10 | 9 | 10 | 11 | 10 | 12 |
| 11 | 13 | 11 | 13 | 11 | 10 |
| 12 | 11 | 12 | 12 | 12 | 13 |
| 13 | 15 | 13 | 15 | 13 | 13 |
| 14 | 14 | 14 | 16 | 14 | 15 |
| 15 | 17 | 15 | 14 | 15 | 14 |
| 20 | 23 | 20 | 21 | 20 | 22 |
| 30 | 29 | 30 | 30 | 30 | 31 |
| 40 | 42 | 40 | 42 | 40 | 40 |
| 50 | 48 | 50 | 52 | 50 | 53 |
| 60 | 60 | 60 | 63 | 60 | 60 |
| 80 | 78 | 80 | 81 | 80 | 84 |
| 100 | 101 | 100 | 103 | 100 | 104 |
| 120 | 121 | 120 | 122 | 120 | 123 |
| 140 | 142 | 140 | 142 | 140 | 142 |
| 160 | 161 | 160 | 166 | 160 | 165 |
| 180 | 181 | 180 | 184 | 180 | 185 |
| 200 | 201 | 200 | 203 | 200 | 206 |
| 220 | 220 | 220 | 223 | 220 | 226 |
| 240 | 240 | 240 | 245 | 240 | 244 |
| 260 | 256 | 260 | 266 | 260 | 267 |
| 280 | 276 | 280 | 287 | 280 | 288 |
| 300 | 296 | 300 | 307 | 300 | 308 |

Fig. 9

| Modulatet monopolar pulse ||||||
| 10Hz || 30Hz || 99 Hz ||
| Set current (mA) | Measured current (mA) | Set current (mA) | Measured current (mA) | Set current (mA) | Measured current (mA) |
|---|---|---|---|---|---|
| 0 | 0 | 0 | 2 | 0 | 1 |
| 5 | 4 | 5 | 6 | 5 | 4 |
| 6 | 6 | 6 | 7 | 6 | 6 |
| 7 | 9 | 7 | 7 | 7 | 7 |
| 8 | 11 | 8 | 9 | 8 | 9 |
| 9 | 8 | 9 | 10 | 9 | 12 |
| 10 | 9 | 10 | 11 | 10 | 10 |
| 11 | 14 | 11 | 10 | 11 | 11 |
| 12 | 12 | 12 | 12 | 12 | 15 |
| 13 | 14 | 13 | 15 | 13 | 14 |
| 14 | 14 | 14 | 16 | 14 | 15 |
| 15 | 18 | 15 | 14 | 15 | 16 |
| 20 | 22 | 20 | 20 | 20 | 21 |
| 30 | 30 | 30 | 33 | 30 | 31 |
| 40 | 40 | 40 | 40 | 40 | 42 |
| 50 | 48 | 50 | 51 | 50 | 53 |
| 60 | 61 | 60 | 62 | 60 | 61 |
| 80 | 80 | 80 | 83 | 80 | 84 |
| 100 | 99 | 100 | 101 | 100 | 104 |
| 120 | 118 | 120 | 124 | 120 | 124 |
| 140 | 139 | 140 | 141 | 140 | 145 |
| 160 | 158 | 160 | 164 | 160 | 165 |
| 180 | 180 | 180 | 185 | 180 | 184 |
| 200 | 197 | 200 | 204 | 200 | 203 |
| 220 | 219 | 220 | 223 | 220 | 225 |
| 240 | 237 | 240 | 244 | 240 | 247 |
| 260 | 260 | 260 | 267 | 260 | 266 |
| 280 | 281 | 280 | 287 | 280 | 288 |
| 300 | 299 | 300 | 307 | 300 | 306 |

Fig.10

| Modulatet bipolar pulse ||||||
| 10Hz || 30Hz || 99 Hz ||
| Set current (mA) | Measured current (mA) | Set current (mA) | Measured current (mA) | Set current (mA) | Measured current (mA) |
|---|---|---|---|---|---|
| 0 | 1 | 0 | 0 | 0 | 0 |
| 5 | 6 | 5 | 7 | 5 | 6 |
| 6 | 8 | 6 | 8 | 6 | 8 |
| 7 | 6 | 7 | 6 | 7 | 9 |
| 8 | 7 | 8 | 8 | 8 | 8 |
| 9 | 8 | 9 | 12 | 9 | 10 |
| 10 | 12 | 10 | 10 | 10 | 12 |
| 11 | 13 | 11 | 12 | 11 | 10 |
| 12 | 14 | 12 | 13 | 12 | 11 |
| 13 | 14 | 13 | 16 | 13 | 13 |
| 14 | 15 | 14 | 14 | 14 | 14 |
| 15 | 17 | 15 | 14 | 15 | 16 |
| 20 | 18 | 20 | 21 | 20 | 20 |
| 30 | 30 | 30 | 33 | 30 | 32 |
| 40 | 41 | 40 | 39 | 40 | 41 |
| 50 | 48 | 50 | 50 | 50 | 50 |
| 60 | 60 | 60 | 60 | 60 | 62 |
| 80 | 78 | 80 | 83 | 80 | 82 |
| 100 | 101 | 100 | 102 | 100 | 101 |
| 120 | 118 | 120 | 122 | 120 | 123 |
| 140 | 142 | 140 | 144 | 140 | 144 |
| 160 | 157 | 160 | 164 | 160 | 162 |
| 180 | 177 | 180 | 183 | 180 | 183 |
| 200 | 201 | 200 | 205 | 200 | 203 |
| 220 | 220 | 220 | 224 | 220 | 226 |
| 240 | 241 | 240 | 246 | 240 | 247 |
| 260 | 259 | 260 | 267 | 260 | 266 |
| 280 | 276 | 280 | 286 | 280 | 286 |
| 300 | 299 | 300 | 305 | 300 | 305 |

Fig. 11

DEVICE FOR NON-INVASIVE ELECTRICAL STIMULATION OF THE SPINAL CORD

This application is the U.S. national phase of International Application No. PCT/RU2016/050077 filed Nov. 29, 2016, which designated the U.S. and claims priority to Russian Patent Application No. 2015156833 filed Dec. 29, 2015, the entire contents of each of which are hereby incorporated by reference.

FIELD

This invention relates to medicine and medical equipment, in general, to the neurology area, and more specifically to noninvasive stimulation of the spinal cord, intended for conducting diagnostic tests and physiotherapy in medical, treatment-and-prophylactic, research medical institutions or in house conditions.

BACKGROUND

The occurrence of spine injuries in Russian Federation is 3.5 cases per year on 10 thousand urban population and tends to growth owing to increase in household, motor transportation, operational injuries, technogenic and natural disasters. Total quantity of patient, becoming disabled people owing to a vertebral and spinal trauma is more than 8000 people per year.

However, this statistics doesn't consider much more extensive contingents of patients with neurologic motive violations in the outpatient sphere of treatment (athletes, patients with infectious, neurotrophic, some psychosomatic diseases and also patients with the motive deficiency, arisen as a result of "surgical aggression"), also needing specialized motive rehabilitation.

In recent years, the electrical stimulation of the spinal cord has proved its efficiency for motor neurorehabilitation. Electrical stimulation of the spinal cord is to conduct a direct (imposing of electrodes is carried out in medical conditions) electrical impact on a spinal cord of the patient.

There are neural networks located in a lumbar thickening of a spinal cord of the person and all mammals, which participate in walking movements. This neural networks (the generator of the locomotion) provide stereotypic rhythmic coordinate activity of muscles of each limb, coordination between the limbs, and also coordination of activity of muscles of limb muscles and a body for movement in space. It has been shown (M. Dimitrijevic et al. Evidence for a spinal central pattern generator in humans. Ann. N.Y. Acad. Sci., 1998, Nov. 16, 860: p. 360-376), that the patients immobilized after injury of the C5-T8 spinal cord segments, having the stimulating electrodes on dura mater of a dorsal surface of a spinal cord under vertebras of T10-T12 and electrically stimulating with a frequency of 25-60 Hz and with an amplitude of 5-9 V, it is possible to cause the step-like movements. Electrical stimulation of the spinal cord, aimed to induce the step-like leg movements, gives a good result in restoring voluntary leg movements and supporting body weight at patients with complete motor damage. It has been shown (Harkema S. et al. Effect of epidural stimulation of the lumbosacral spinal cord on voluntary movement, standing, and assisted stepping after motor complete paraplegia: a case study. The Lancet. 2011. T. 377. No 9781. C. 1938-1947), that for a patient with a complete motor break of the spinal cord at the level of the C7-T1 segments, chronic epidural electrical stimulation at the level of L1-S1 segments with a frequency of 40 Hz and an amplitude of less than 5-10 V, carried out simultaneously with locomotor training for 7 months after implanting the electrodes on the dorsal surface of the spinal cord, has led to a positive effect. This electrical stimulation was carried out three years after the injury. After that, the patient was able to stand alone for 4-25 minutes against the background of continuous stimulation of the spinal cord. The patient could also, lying on his back, make some arbitrary movements of the legs against the background of continuous electrical stimulation of the spinal cord, namely, bend or unbend in the knee or ankle joints of the right or left leg.

RU Patent Number 2204423 C2, published 20 May 2003, describes a method of treating patients with chronic spinal cord damage. In this method, the electric stimulation of the lumbar spinal cord thickening is carried out with the help of electrodes applied to the dura mater of the spinal cord and causes legs movements with the facilitated position of the patient lying on his back or on his side with legs suspended on the swing frames. This method of treating patients with chronic spinal cord injury is invasive and consists of applying stimulating electrodes to the dura mater of the spinal cord followed by electrical stimulation of the spinal cord below the level of its damage. The implementation of the treatment method requires surgery for the implantation of electrodes and specific medical care for the entire period of operation of stimulating electrodes to prevent inflammatory reactions, electrode rejection.

RU Patent Number 2471518 C2, published 1 Oct. 2013, describes a method of electrostimulation of the spinal cord, consisting of a transcutaneous electrical effect on the spinal cord. An important feature of stimulation is its painlessness for a person. The low-frequency bipolar pulse (5-30 Hz) is modulated by the high-frequency component (2.5 kHz and higher), which ensures painless stimulation. Due to the use of an electric pulse of a special form, it is possible to deliver painlessly currents of large amplitude, which effectively penetrate from the skin surface into the structures of the spinal cord and initiate involuntary pacing movements in healthy subjects.

The main advantage of the transcutaneous stimulation method is the possibility of electrostimulation with the help of cutaneous electrodes in contrast to the direct electrostimulation, which is carried out with the help of electrodes applied to the dura mater of the spinal cord and which requires surgical intervention to accommodate electrodes on the spinal cord surface and subsequent postoperative support with the risk of any surgical and postoperative side effects.

A non-invasive neuromodulator is also known to facilitate recovery of motor, sensory, vegetative, sexual, vasomotor and cognitive functions (WO2013071307 A1, published on May 16, 2013).

The device consists of a processor, signal generator, electrodes and a storage device. The device generates bipolar pulses with a frequency of 0.5-100 Hz and an amplitude of 0.5-200 mA, the pulses are filled with a high-frequency component with a frequency of 5 or 10 kHz. Pulses can be applied cutaneous, paraspinal in the neck, thoracic or lumbar spine regions and can be effective for the treatment of numerous neurological diseases that cause movement disorders.

Researches on animals with spinal cord injuries, conducted in laboratory conditions modeling pathology should be preceded by the use of electrical stimulation of the spinal cord in therapeutic measures, the choice of stimulation parameters should be based on the available evidence of their effectiveness. Laboratory studies on animals have convincingly shown that electrical epidural stimulation of the lumbar region of spinal cord is a nonspecific activator of the generators of step-like movements (Courtine G. et al. Transformation of nonfunctional spinal circuits into functional states after the loss of brain input. Nature Neuroscience. 2009. T. 12. No 10. C. 1333-1342; etc.). The locus of the spinal cord, optimal for locomotion, are segments of the spinal cord L2-L4. Locomotor movements are not caused, but all the extensor muscles of the hind limbs are activated, with help of the electrical epidural stimulation of the S1-S2 segments of the spinal cord in animals, thus the stimulation of the S1-S2 segments of the spinal cord should be effective to maintain body weight, vertical stance. The frequency of electrical stimulation of 5 Hz is effective to triggering motions of the whole spinal cord in the absence of supraspinally effects (Gerasimenko Y. P. Features of the formation of locomotor patterns at a decerbered cat during epidural stimulation of the spinal cord. Russian journal of physiology. I. M. Sechenova, 2003, vol. 89, No. 9 1046-1057). The 40 Hz frequency of ESSM is effective for triggering locomotion and supporting body weight with complete spinal cord break in the lower thoracic region (Ichiyama R M et al., Hindlimb stepping movements in complete spinal rats induced by epidural spinal cord stimulation, Neuroscience Letters, 2005. v. 383, p. 339-344).

Thus, it is necessary to act on several regions of the spinal cord to restore arbitrary movements in full, not only rhythmic leg movements, but also independent walking with the control of the balance of body weight, while the above-stated sources of information describe the impact only at one region of the spinal cord in a certain frequency range revealing ways and devices for stimulation of the spinal cord.

US 20140180361 A1 describes a neurostimulator, which allows to simultaneously stimulate up to four groups of electrodes on the spinal cord. However, this device is intended for invasive stimulation of the spinal cord, when the electrodes are attached on the dura mater of the spinal cord. The use of this device is not possible without surgical intervention.

At the same time, the method of transcutaneous electrostimulation of the spinal cord disclosed in RU 2529471 C2, is known, published on 27 Sep. 2014. The method involves the action of a sequence of electric rectangular bipolar pulses in the form of meanders with a frequency of 5-40 Hz, a duration of 0.5 ms and a carried frequency of 10 kHz on the spinal cord of the patient lying on their side, with legs suspended in the swing frames, wherein impact produces at the region of the thoracic (T11-T12), cervical (C4-C5) and lumbar (L1-L2) vertebrae. The effect is carried out by pulses with an amplitude in the range of 40-200 mA, depending on the region of the spinal cord. The pulses in the burst have a phase shift of 0.1-0.5 ms. As an apparatus implementing the known method, an electrostimulator comprising three galvanically isolated stimulation channels with an electrode system, connected accordingly to the signal control unit, the microcontroller, the signal shaper, and also to units for measuring amplitude and indication and to power unit. The known method activates the movements of the patient's legs in the hip, ankle and knee joints.

RU Patent Number 2545440, publ. Mar. 27, 2015, describes a method of non-invasive electrical stimulation of the spinal cord, in which the impact is made on the areas of the spinal cord, located directly above the spine, between the spinous processes, and on the areas above the roots of the spinal cord, located symmetrically to the right and left of the spine, while the pulses are fed to the specified areas with a given sequence. To do this, use a device that contains a matrix in the form of electrodes, an electrical pulses shaper, a control unit, a microcontroller with software, a signal former, a unit for measuring the amplitude of the current at the input of the electrodes, and a block for indicating the required parameters.

The disadvantage of non-invasive stimulation of the spinal cord is the permissible uncertainty in the location of the electrodes relative to the segments and roots of the spinal cord, which must be stimulated.

With modern stimulation technology, the reference point in choosing the location of the electrodes on the skin is the spinous processes of the vertebrae of the spinal cord and the ribs. Both are palpable under the skin. A layer of subcutaneous adipose tissue or significantly developed paravertebral muscles can make it difficult to accurately orient. In addition, the characteristics of individual development, trauma and disease lead to different deviations from the norm in the structure and location of the spine and ribs.

A reliable way to determine the position of electrodes on the skin relative to the spinal cord is to register reflex muscular responses to single pulses applied to the electrode—the responses in these or those muscles are determine the position of the stimulating electrode to within one segment.

A method is known (Krenn M., Toth A., Danner S. M., Hofstoetter U. S., Minassian K., & Mayr W. (2013). Selectivity of transcutaneous stimulation of lumbar posterior roots at different spinal levels in humans. BiomedTech, 58,1) which consists in transcutaneous stimulation of the spinal cord and dorsal roots of the spinal cord in the region of the Th11-Th12 vertebrae using biphasic pulses (2×1 ms) with an intensity of up to 125 mA. The method allows to record reflectory leg muscles contractions for each pulse, the amplitude and shape of which depends on the location of the application.

However, this method causes reflex responses of the leg muscles, but does not cause leg movements and does not provide control of these movements.

A stimulating electrode is placed on the skin above the spinal cord. A single unmodulated pulse is applied. The muscles begin to contract at a certain intensity of the pulse. Reduction of muscles can sometimes be observed visually.

The method of surface electromyography can be used to quantify the strength of muscle contraction. Each segment of the spinal cord innervates a specific set of skeletal muscles. The segment-muscle ratio is well known. It can be concluded that spinal cord segments L2-L3 are under the electrode, if the electrode is between the spinous processes of the vertebrae T11 and T12 and with stimulation at this place actively reduced mm. vastus lateralis, rectusfemoris and to a lesser extent—mm. hamsterimg, tibialisanterior. The ratio of the "vertebra-segment" of the spinal cord may differ from the normal due to the characteristics of the human onto- and phylogenesis. Finally, can be difficult to identify a vertebrae because of spinal injuries, etc.

It is known that single rectangular pulses are required to register standard reflex responses in muscles. None of the known stimulators for transcutaneous electrical stimulation of the spinal cord generates such impulses.

The rectangular pulses are generated by industrial stimulators designed for neuroscience research, but in this case, one device is required for the precise positioning of the electrodes and one device for the rehabilitation procedure consisting in electrical non-invasive stimulation of the spinal cord. In addition, industrial stimulators generates pulses with an amplitude of not more than 100 mA. This current amplitude is usually not enough to cause a reflex response in the leg muscles with transcutaneous stimulation of the spinal cord because of the degenerative processes occurred in the spinal cord and in the muscles due to disease or injury.

The experience of using devices for transcutaneous stimulation of the spinal cord showed that the maximum current amplitude for which they are designed is 200 mA. Stimulation in such an amplitude range is quite effective in experiments on healthy volunteers and in the rehabilitation of patients with mild trauma or spinal cord disease, but this current amplitude is not enough to cause a locomotor response to rhythmic stimulation of patients with significant and long-term trauma or spinal cord disease. This is associated to the high degree of degeneration of the spinal cord and muscles because of trauma or disease. It is necessary to increase the pulse energy, either by increasing the amplitude of bipolar pulses modulated by high frequency, or by stimulating monopolar pulses, modulated or not modulated, in order to cause a locomotive response. Monopolar pulses will be painless for such patients because of their lack of sensitivity below the place of the disease or injury, where the pulses are applied, but monopolar pulses leave on the skin a potential that can cause a burn.

Thus, at the technical level, a device for non-invasive stimulation is not known, which combines the possibility of a two-stage impact to determine the localization of the stimulating electrodes by single rectangular pulses with a maximum current amplitude more than 200 mA, and directly to spinal cord stimulation are modulated by pulses of different shapes simultaneously into several segments of the spinal cord and the roots of the spinal cord with the choice of frequency of stimulation and modulation frequency.

SUMMARY

The object of the present invention is to create a multifunctional device for non-invasive stimulation of the spinal cord, generating rhythmic bipolar and monopolar pulses of rectangular shape, modulated by high frequency, as well as monopolar unmodulated pulses of rectangular shape, with a maximum current amplitude of 300 mA, leaving no potential on the skin, allowing to stimulate the spinal cord to at least three region of the spinal cord simultaneously (cervical, thoracic and lumbar regions), as well as stimulate the roots of the spinal cord at least on one region of the spinal cord, as well as devices for studying the functions of the intact and diseased spinal cord.

The technical effect of the present invention as disclosed herein is to increase the efficiency of the rehabilitation process of patients with spinal cord pathologies, of patients with severe motor disorders, including the restoration of voluntary movements in full, without surgical intervention for the implantation of electrodes, as well as without the risks associated with a foreign body implanted on the surface of the spinal cord.

An additional technical effect of this invention is the expansion of the arsenal of technical means intended for transcutaneous stimulation of the spinal cord.

The technical effect is achieved by the fact that the spinal cord electrostimulator comprises five stimulation channels with an electrode system. Each of channels includes a series-connected voltage converter, a current generator and an output signal shaper. Each of channels is configured to be able to generate the following rectangular pulses: single monopolar, rhythmic monopolar, rhythmic modulated monopolar, rhythmic modulated bipolar—with a stimulation frequency in the range of 1-99 Hz, with a current amplitude from 1 mA to 300 mA and a modulation frequency from 4 to 10 kHz. The inputs of each channel are connected to the microcontroller, which is itself connected to an indication unit, a control unit and a radio module. Herewith the microcontroller is configured to trigger at least one stimulation channel, to select a triggering mode rt independently for each of the stimulation channels, to control each of the stimulation channels with parameters of the pulses selected from the following: shape of the pulses, frequency of the stimulation, which may change in steps of 1 Hz or higher, modulation frequency which may change in steps of 1 kHz or higher, current amplitude, which may change in steps of 1 mA or higher and pulse duration, which may change in steps of 0.1 ms or higher.

In accordance with at least one embodiment, the microcontroller is configured to be able to trigger the stimulation channel depending on the activity of another stimulation channel, setting the delay time and duration of a series of pulses.

In accordance with at least one embodiment, the microcontroller is configured to select the triggering mode between a single-time mode with a passive phase of depolarization and a continuous mode with active type of a phase of depolarization.

In accordance with at least one embodiment, the electrical stimulator is synchronized with external devices, with a synchro-input, for example, with devices for recording the induced motor response.

In accordance with at least one embodiment, the electrostimulator is further connected to a computer.

In accordance with at least one embodiment, triggering of at least one stimulation channel, the selection of the triggering mode independently for each of the stimulation channels, the control of each of the stimulation channels by the parameters of the rhythmic pulses is carried out by means of the computer and/or the control unit and the indication unit.

The electrostimulator is a tool for studying the functions of the intact and diseased spinal cord, since said electrostimulator provides different forms of pulses, allows creating different stimulation scenarios, allows to synchronize each of the channels with external equipment, including with the recording equipment. This technical effect allows to apply this stimulator in fundamental and applied scientific researches.

The ability to simultaneously influence on 5 segments of the spinal cord, or on 3 segments of the spinal cord and 2 roots of the spinal cord, or 1 segment of the spinal cord and 4 roots of the spinal cord, etc. with the help of 5-stimulation channels will allow to restore arbitrary movement in full.

The effectiveness of spinal cord stimulation increases as a result of a more precise localization of electrodes to the segments of the spinal cord due to an additional primary effect for muscle activation, while the name of the activated muscles and the degree of response of the activated muscle are unambiguous signs of electrode localization relative to the segment of the spinal cord.

The ability to vary the setting of modes, to select the channels of stimulation, their parameters, in particular, the adjustment of the amplitude range of the output current, the stimulation frequency and the modulating frequency, depending on the degree of damage to the spinal segment, contributes to the rapid and qualitative restoration of the functional capabilities of the patient.

The amplitude range of the output current of single rectangular pulses is larger than that of known analogues, which allows to cause a locomotor response to rhythmic stimulation of patients with significant and long-term trauma or spinal cord disease.

All rhythmic pulses are designed to trigger a locomotor response or trigger a tonic response in the muscles, which is necessary to maintain a vertical posture. They are ranked as follows: monopolar unmodulated, monopolar modulated, bipolar modulated (in order of the effectiveness reduction and pain decrease).

The property of the stimulator to provide zero potential on the skin at the site of electrodes application helps prevent a possible skin burn in the case of a large pulse amplitude.

BRIEF DESCRIPTION OF THE DRAWINGS

Many aspects of the disclosure can be understood with reference to the following drawings.

FIG. 3A. Unmodulated pulse with active depolarization phase.

FIG. 3B. Unmodulated pulse with passive depolarization phase.

FIG. 3C. Modulated monopolar pulse with active depolarization phase.

FIG. 3D. Modulated monopolar pulse with passive depolarization phase.

FIG. 3E. Modulated bipolar pulse.

Pos. 1—m. tibialis, right.
Pos. 2—m. gastrocnemius, right.
Pos.3—m. biceps, right.
Pos. 4—m. rectus, right.
Pos.5—m. vastuslat, right.
Pos. 6—m. vastuslat, left.
Pos. 7—m. biceps, left.
Pos. 8—m. rectus, left.
Pos. 9—m. tibialis, left.
Pos. 10.—m. gastrocnemius, left.
Pos. 11—goniometer at the knee, right.
Pos. 12—goniometer at the knee, left.
Pos. 13—mark of the 1st channel of the stimulator.
Pos. 14—mark of the 3rd channel of the stimulator.
Pos. 15—mark of the 4th channel of the stimulator.

Figure 6:
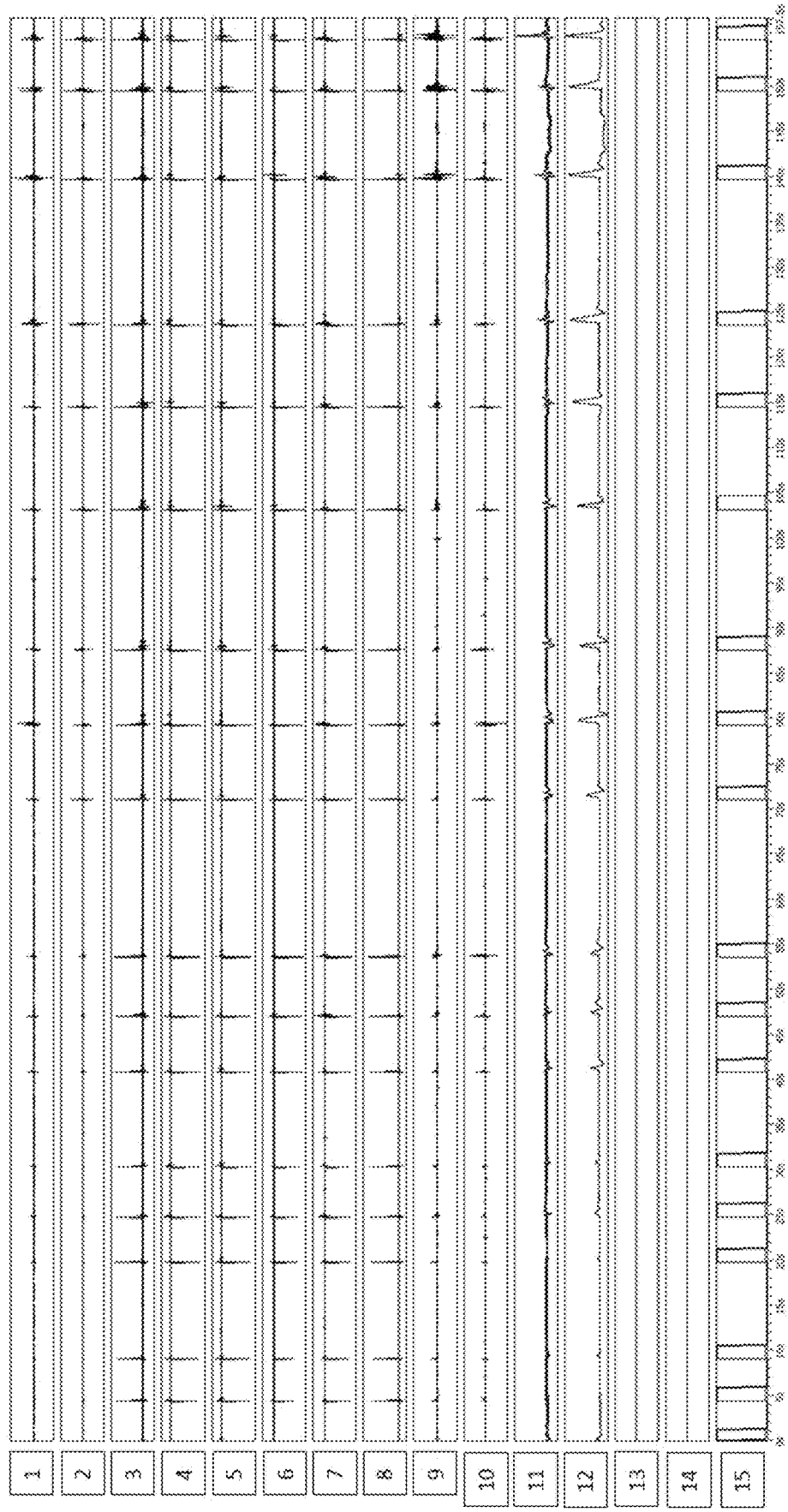
FIG. 6 depicts the original recording of the registration of motor responses caused by transcutaneous stimulation of the spinal cord at the coccyx region (CO vertebrae) by single monopolar unmodulated pulses of intensity 1-50 mA. Subject DG.
Figure 7:
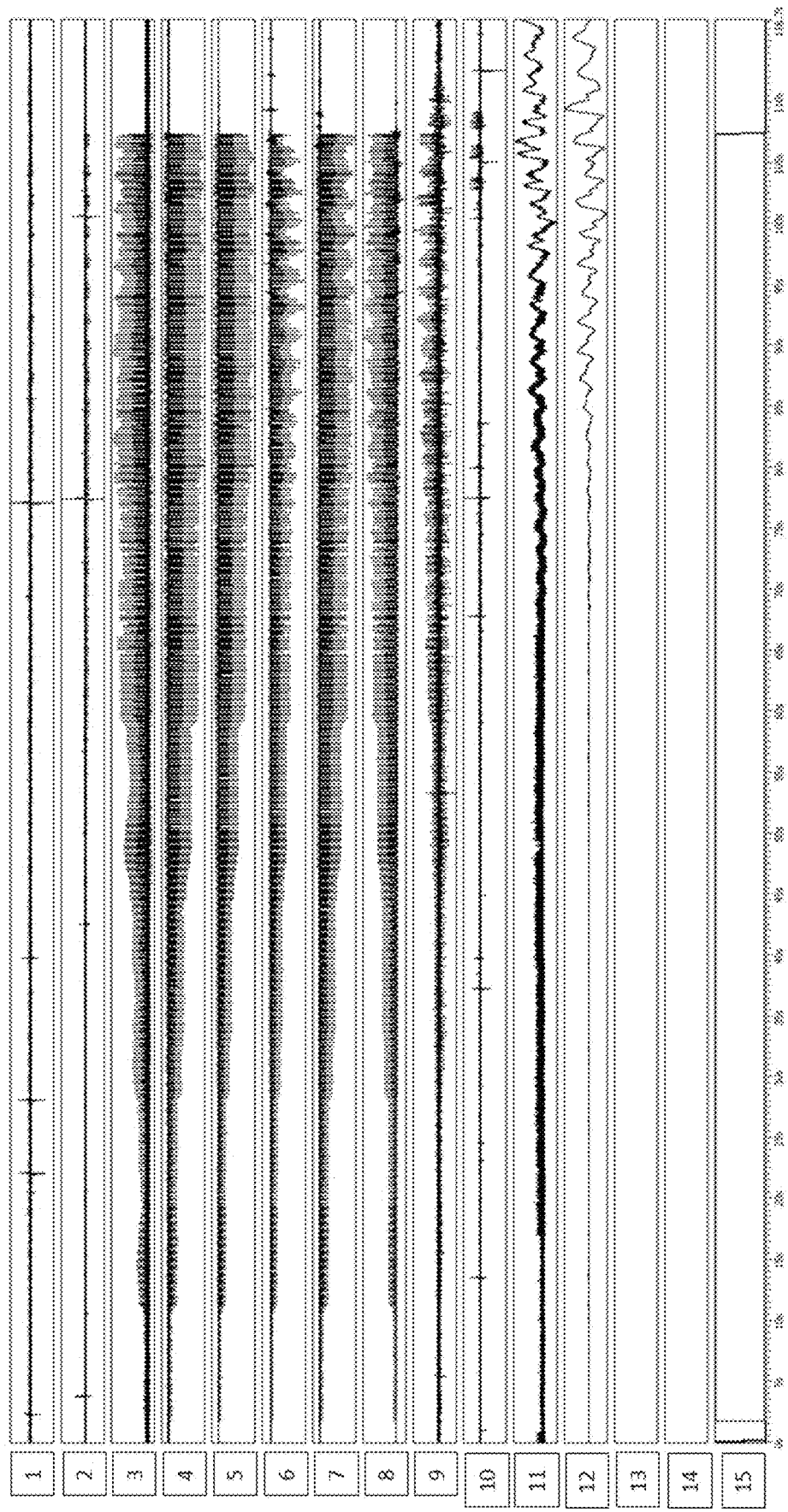

FIG. 7 depicts the original recording of the registration of motor responses caused by transcutaneous stimulation of the spinal cord at the coccyx region (CO vertebrae) by continuous monopolar modulated pulses with a frequency of 5 Hz and a modulation frequency of 10 kHz, intensity of 1-45 mA. Subject DG. The designations are the same as in FIG. 6.

Figure 8:
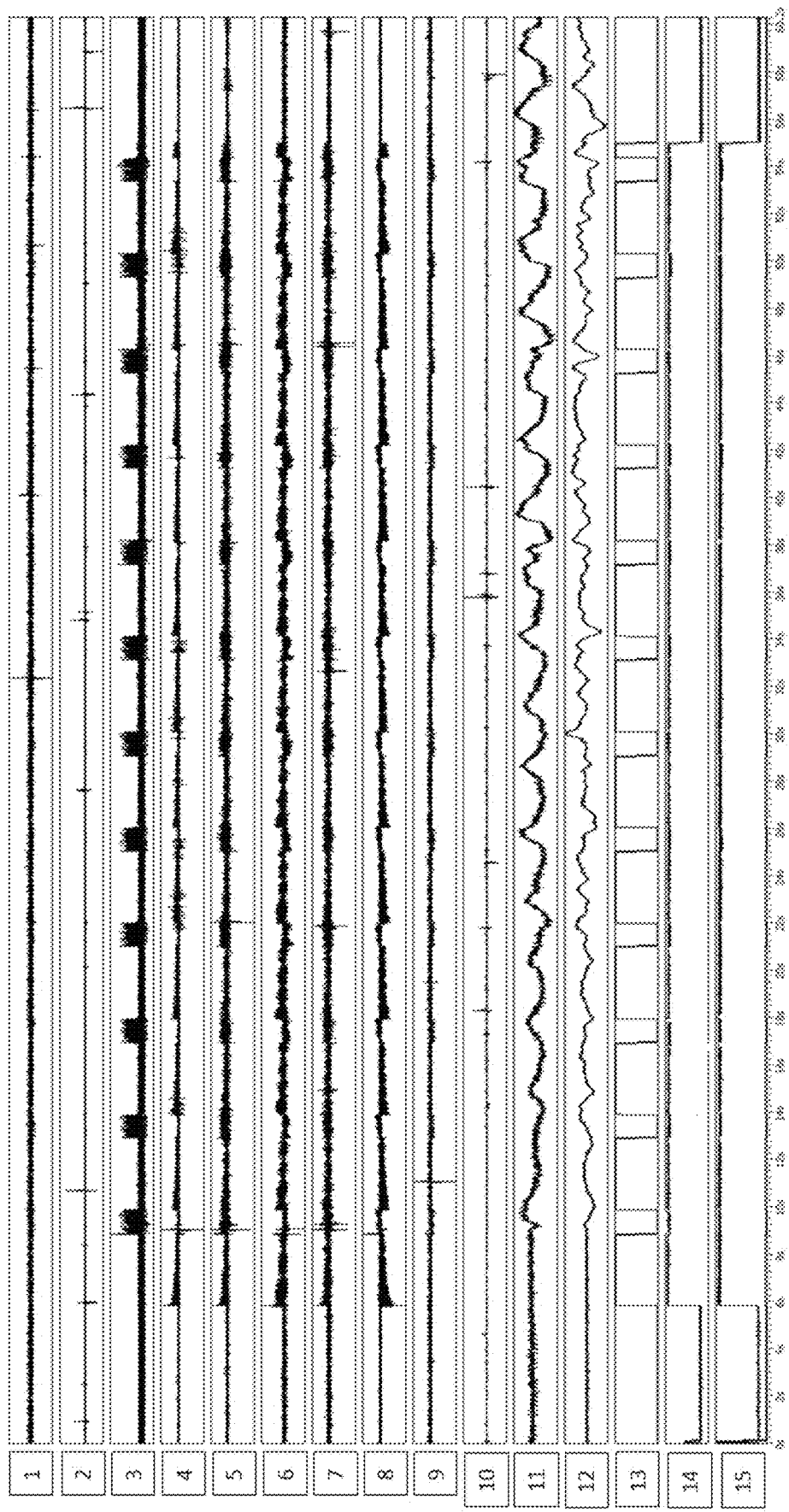

FIG. 8 depicts the recording of the motor responses caused by transcutaneous stimulation of the spinal cord at two regions of the spinal cord along four stimulation channels: the electrodes were attached along the midline of the vertebrae between the vertebrae Th11-Th12 (the 3rd stimulator channel), above the vertebrae Co (4th stimulator channel), above the roots of the spinal cord to the right and left of the vertebra Th11 (the 1st and 2nd channels of the stimulator). Used bipolar modulated mode with frequency of 30 Hz and a modulation frequency of 10 kHz for all channels. The 1st and 2nd channels of the stimulator were triggered antiphase, zero current by $1^{st}$ channel to vary the duty cycle and use only the right leg (1 sec. of stimulation of the 2nd channel, then 3 sec. delay). An current of 15 mA on 2-4 channels. Subject DG. The designations are the same as in FIG. 6.

FIG. 9-11 shows tables describing the ratio between the set and measured currents on one of the channels of the stimulator.

Table. 1A. shows the ratio between the set and the measured current during testing the 1st channel of the electrostimulator at frequencies of 10, 30, 99 Hz. Unmodulated monopolar pulse.

Table. 1B. shows the ratio between the set and the measured current during testing the 1st channel of the electrostimulator at frequencies of 10, 30, 99 Hz. Modulated monopolar pulse. Modulation frequency of 10 kHz.

Table. 1C. shows the ratio between the set and the measured current during testing the 1st channel of the electrostimulator at frequencies of 10, 30, 99 Hz. Modulated bipolar pulse. Modulation frequency of 10 kHz.

TABLE OF SYMBOLS 1-5. Identical channels of the stimulator.
6. Current Generator.
7. Voltage converter.
8. Output signal shaper.
9. Microcontroller.
10. Indication unit.
11. Keyboard.
12. Radio module of the electrostimulator.
13. Power supply.
14. Rechargeable battery.
15. The electrostimulator.
16. The computer.
17. The USB port of the computer.
18. The radio module of the computer.
19. A patient.
20-24. Active electrodes, cathodes.
25, 26. Passive electrodes, anode.
27. Power button.
28. Emergency stop button.
29. Panels enable and control the activity of five channels.
30. Channel enable button.
31. Channel ready indicator.
32. Two-color channel activity indicator (current greater than 0 mA).
33. Channel selection button for setting work.
34. Button to select the operating mode of the selected channel.
35. Button to select pulse frequency for the selected channel.
36. Button to select the pulse duration for the selected channel.
37. Button to select current amplitude for the selected channel.
38. Indication of resistance under the electrode to the selected channel.
39. LCD alphanumeric display, LED panel, which displays the selected and measured values.
40. Connector to the 220 V network.
41. Battery charging button

DETAILED DESCRIPTION

The electrostimulator (FIG. 1, pos. 15) comprises five identical stimulation channels (1-5). Each of said stimulation channels contains connected in series a current generator (6), a voltage converter (7), an output signal generator (8). Each of the five stimulation channels is connected to a microcontroller (9), which is itself connected to an indication unit in the form of alphanumeric display (10) and a keyboard (11). The microcontroller is also connected to a radio module (12). The electrical stimulator contains a power supply (13) and a battery (14).

The microcontroller is capable of triggering at least one said stimulation channel, selecting a triggering mode independently for each of said stimulation channels, controlling each of said stimulation channels with pulse parameters selected from the following: pulse shape, stimulation frequency, which may change in steps of 1 Hz or higher, modulation frequency, which may change in steps of 1 kHz or higher, current amplitude, which may change in steps of 1 mA or higher, and pulse duration, which may change in steps of 0.1 ms or higher.

In accordance with at least one embodiment, the electrical stimulator can be connected to a computer (16) either through a computer USB port (17) or via a radio channel via a computer radio module (18).

Figure 2:
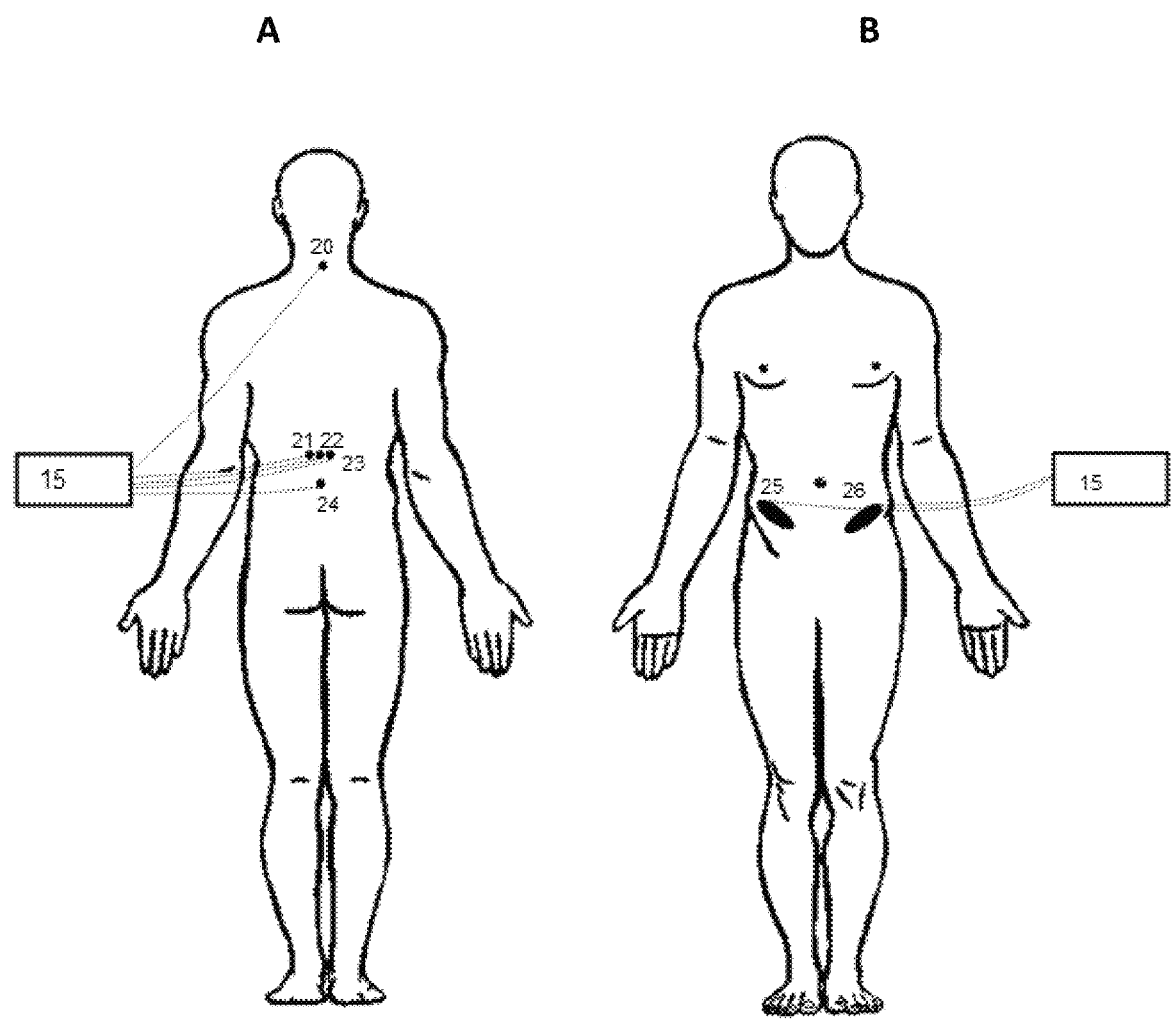
FIG. 2 illustrates an example of the electrodes location on the human body
A—back view, B—front view.

Each of the five channels of the electrostimulator is connected to the electrodes on the patient's body (19) by means of wires (FIG. 2). The electrodes are made of specific geometry to be attached between the spinous processes or exactly above the roots of the spinal cord, for example, round diameter of about 2 cm.

The active electrodes (cathodes) are attached epicutaneously paraspine in the neck, thoracic, lumbar region or in the coccyx and/or paravertebral in the projection of the roots of the spinal cord (FIG. 2; Pos. 20-24). Passive electrodes (anodes) are attached, for example, in the abdomen, above the iliac bones (25, 26). Passive electrodes are a "common ground" for all active electrodes.

Each of the electrostimulator channels generates pulses in the range from 1 mA to 300 mA, in 1 mA steps. Current amplitudes less than 40 mA can be used to determine the thresholds of the muscles that respond to stimulation of the spinal cord. The use of currents greater than 250 mA allows to induce the response of those structures and conducting pathways of the spinal cord whose excitability is reduced due to disease or injury and does not respond to pulses less than 250 mA.

The electrostimulator is synchronized with external devices with a synchro input, which can be designed, for example, to record the induced motor response.

Figure 3A:
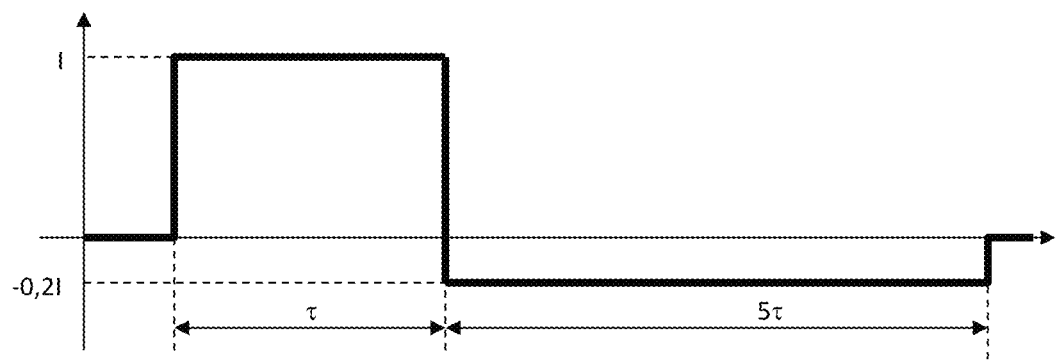
FIG. 3A-3E depicts various forms of pulses affecting the spinal cord, with I—a given current, τ—pulse duration, T—is the pulse modulation period.
Figure 3B:
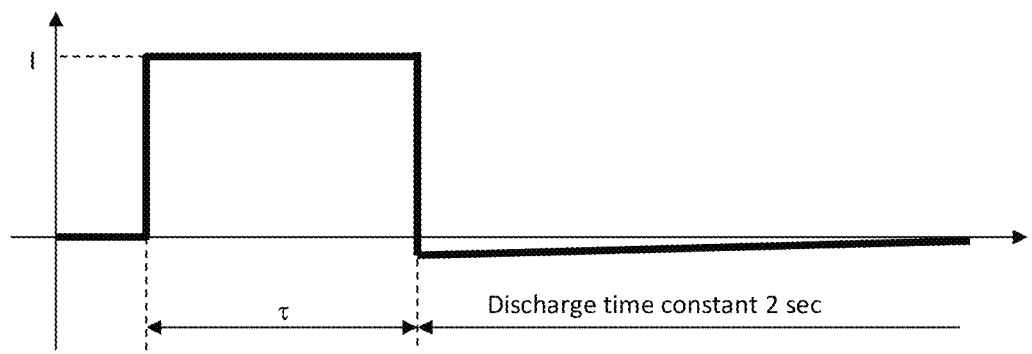
Figure 3C:
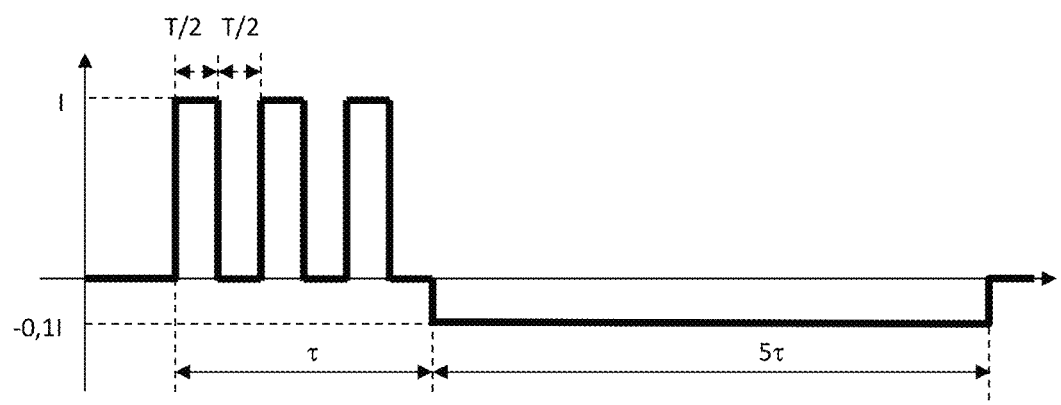
Figure 3D:
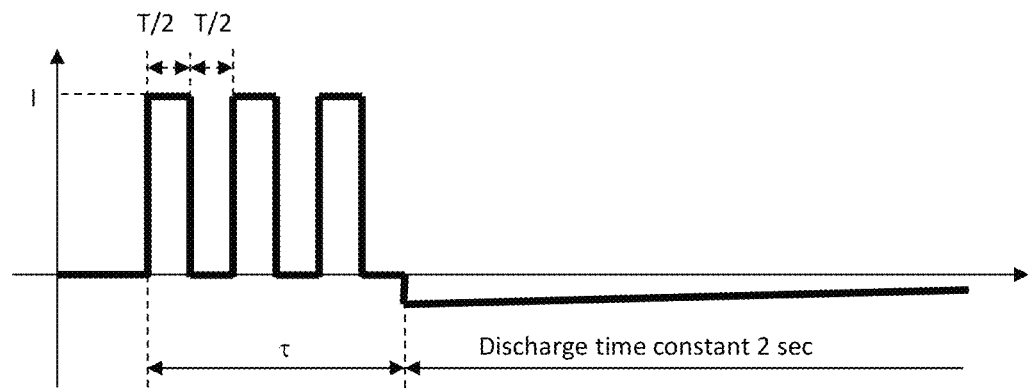
Figure 3E:
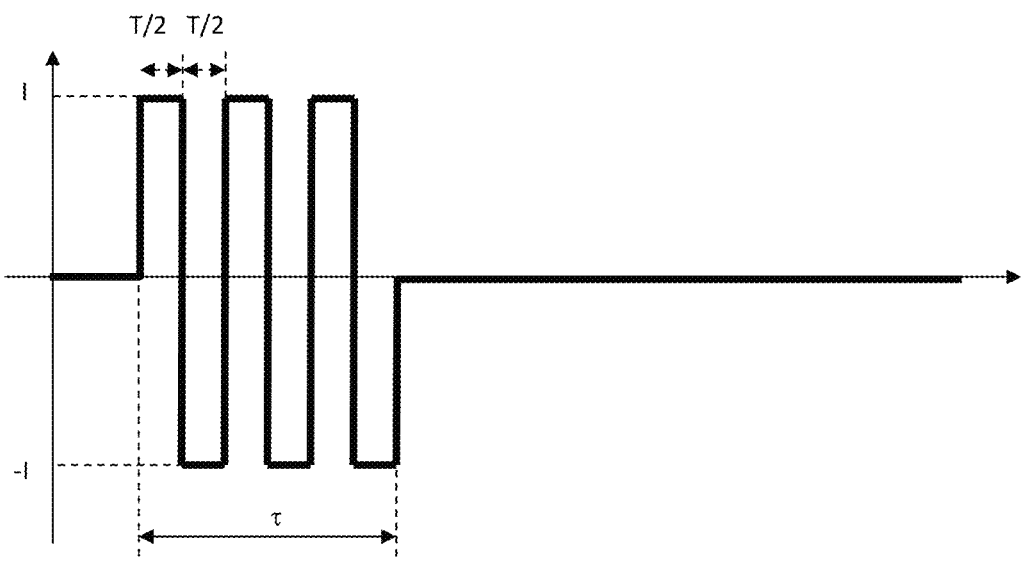

The pulse can be one of three forms: a rectangular unmodulated monopolar (FIG. 3A, 3B), a rectangular modulated monopolar (FIG. 3C, 3D), a rectangular modulated bipolar (FIG. 3E). The possibility of generating three types of pulse by the electrostimulator allows using it for different purposes: for examining the conducting pathways of the spinal cord in patients or normal (for healthy volunteers, for intact spinal cord function studies), for the treatment/rehabilitation of patients with different degrees of spinal cord damage.

Unmodulated monopolar pulses are used to invoke responses of structures lying below the stimulation site (study). Modulated bipolar pulses are used in experiments to induce step-like movements in the spinal cord stimulation in healthy volunteers, as they are painlessly carried by people with normal sensitivity. A continuous sequence of modulated bipolar pulses, or modulated monopolar pulses, or unmodulated monopolar pulses are used to trigger step-like movements in the spinal cord stimulation of patients with spinal cord disease/injury (the choice of pulse shape depends on excitability of the patient's spinal cord, of the patient's pain sensitivity, etc.).

The modulation frequency can be set from 4 to 10 kHz in steps of 1 kHz. Thus, the claimed electrostimulator can be used to study the effect of the modulation frequency of monopolar and bipolar rectangular pulses on the characteristics of the motor response, etc.

The pulse repetition rate can be set from 1 Hz to 99 Hz in steps of 1 Hz. Thus, the electrostimulator can be used to study the effect of the frequency of monopolar non-modulated rectangular pulses, monopolar modulated rectangular pulses and bipolar modulated rectangular pulses on the characteristics of the motor response, etc.

The average current produced by the claimed stimulator for each channel (constant current component) is zero. Therefore, the unmodulated pulse and the modulated monopolar pulse have a depolarizing phase of the reverse polarity current (depolarizing "tail") (FIGS. 3A-3E). There are two types of depolarizing phase: passive or active. The passive phase is characterized by a small depolarizing current and a long duration of the depolarizing phase: the time constant of the current decay is 2 s (FIG. 3B, 3D). The active depolarizing phase is characterized by a relatively large polarizing current, the values of ⅕ of the set current for the unmodulated pulse and ⅒ of the set current for the modulated monopolar pulse (FIG. 3A, 3C) and a relatively short duration of the depolarizing phase, equal to 5 pulse durations.

Only one channel is active at a time. This means that when there is a pulse on one channel, there is no pulse on all other channels in this fraction of the millisecond. This is done in order to avoid summation of pulses, to protect the patient from unpredictable currents values.

Simultaneous stimulation on 5 channels is possible.

The time of the channel activity consists of the pulse duration and time of the active depolarizing phase, if any. Thus, the total frequency of all channels is limited. The total time of active state of all the channels per time unit does not exceed it. For example, if all 5 channels produce modulated monopolar pulses of 1 ms duration with active depolarizing phase and the same pulse repetition rate, this frequency does not exceed 1000 ms/(6 ms*5 channels)≈33 Hz.

Control for each of the stimulation channels (1-5) of the electrostimulator (15), triggering one of said stimulation channel (1-5), selecting the triggering mode independently for each of the stimulation channels (1-5) can be either only autonomous, from control and indication units located on the front panel of the electrostimulator (15), or from the controls on the front panel of the electrostimulator (15) and from a computer (16). In the second case, the electrical stimulator (15) must be connected to the computer (16) either by a USB cable or by a radio channel. The buttons on the panel of the electrical stimulator, selecting the controlled channel, stimulation mode, pulse amplitude, etc. are the operating controls.

Figure 4:
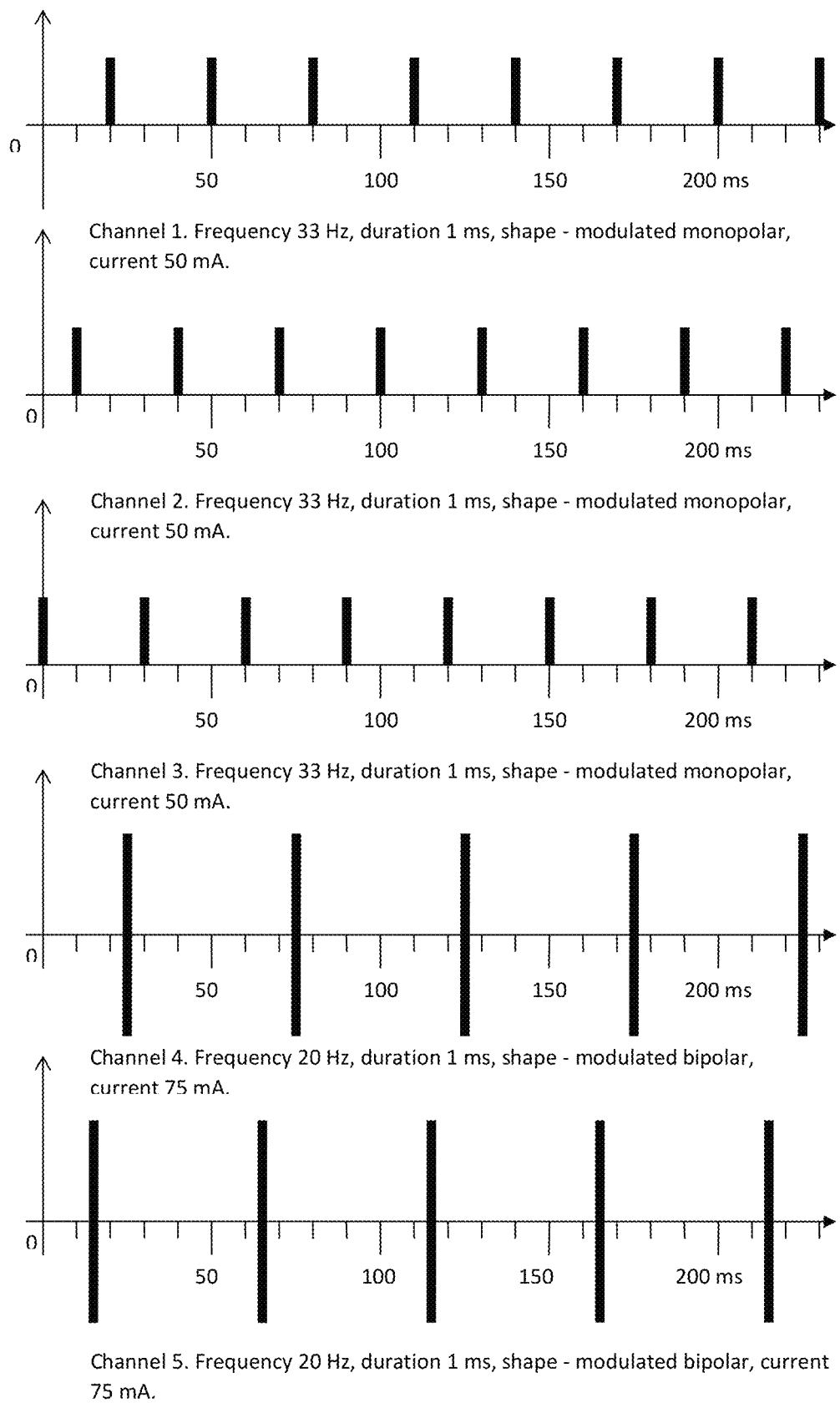
FIG. 4 depicts an example of a possible temporal distribution of pulse packets along five stimulator channels.

FIG. 4 shows a schematic example of the time distribution of pulse packets across all channels.

Thus, in some embodiments, the electrostimulator is configured to select a parameter setting, either autonomously or remotely by the computer.

The ability to control the electrostimulator through the computer allows, at first, to set up complex stimulation scripts, which can be used both in the study and in treatment; secondly, to preserve the characteristics of stimulation (amplitudes, frequencies, order of switching channels, etc.) in the computers memory for analysis and further use in the treatment, etc., and can also be copied to another computer, to another device, similar to the claimed; at third, it allows to synchronize the operation of the stimulator with other stimulating, recording and other devices controlled by the computer; in the fourth, the ability to adjust a part of the parameters both on the computer and on the stimulator panel provides the convenience of working with the stimulator: the stimulator is located in close proximity to the patient/subject (at a distance of the length of the wires of the stimulating electrodes), thus it is possible to change the parameters of the stimulating current depending on the reaction of the patient/subject, even when the main control of the electrostimulator is from a computer, which can be at a considerable distance from the electrostimulator, limited by the length of the USB cable or the range of the radio channel.

The claimed device has two triggering modes of the stimulation: a one-time triggering and a continuous triggering. In this case, the modes of each of the stimulation channel are selected independently. That is, a part of the stimulation channels can work with the one-time triggering "by hand", some in a continuous triggering mode.

A passive type of depolarization phase is set in the one-time triggering modes. The charge flowing in the one-time triggering modes during the series of pulses does not exceed 1 mC, i.e. the number of pulses in the series does not exceed a certain value, depending on the given current, shape and pulse duration. For example, the number of pulses in a series does not exceed 1000 µC/(100 mA*0.5*1 ms)=20 pulses, when stimulated by modulated monopolar pulses 100 mA, duration 1 ms.

The time between consecutive triggering is not less than 5 seconds in the one-time triggering modes.

The stimulation current can be limited if these conditions are not met in the one-time triggering modes.

The one-time triggering mode of the stimulation can be used, for example, to register the reflex activity of muscles to stimulate the spinal cord.

An active type of depolarization phase is set in the continuous triggering modes.

The continuous triggering mode of the stimulation can be used, for example, for transcutaneous stimulation of the spinal cord.

Any of the stimulation channels can work in the external triggering mode. In this case, the stimulation channel outputs current pulses or not, depending on the state of one of the two input logic signals:

the stimulation channel operates at a high level of the first sync signal and is silent at a low level of this signal;

the stimulation channel operates at a low level of the first sync signal and is silent at a high level of this signal;

the stimulation channel operates at a high level of the second sync signal and is silent at a low level of this signal;

the stimulation channel operates at a low level of the second sync signal and is silent at a high level of this signal.

The choice of one or another option is made independently for each channel. The variety of possibilities of triggering the stimulator from different types of sync-signal makes each of the five channels compatible with almost any external device having a sync input.

The presence of 5 channels and peculiarities of their triggering (from the button on the stimulator panel, from the computer, from the other stimulator channel, from the external device to the sync pulse) allows to stimulate from 1 to 5 regions of the spinal cord (simultaneously or sequentially), to program complex spinal cord stimulation scripts, synchronize stimulation with the operation of external devices (recording or stimulating).

Figure 5:
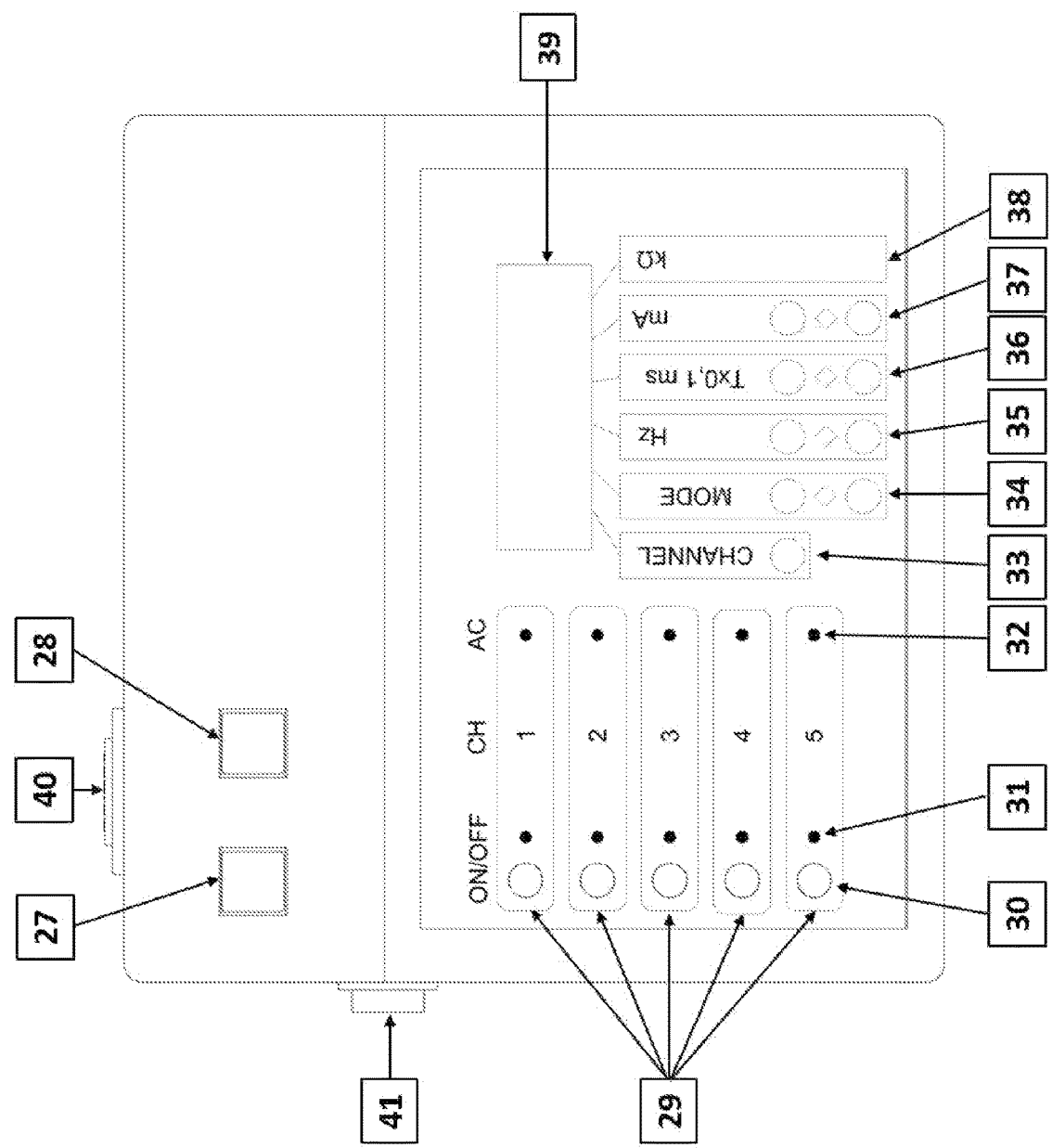
FIG. 5 depicts an example of the execution of the front panel of the stimulator.

One of the variants of the stimulators corresponding to the technical solution of the device is shown in FIG. 5. The external panel of the stimulator contains the power-on button (27), the pause-off button on all channels at once (28), the same activation and activity panels for each of the five channels (29). There is a triggering button for each stimulation channel (30), a LED for the stimulation channel ready to work, glowing when the stimulation channel is turned on (31) and an LED two-color current indicator glowing when the stimulation channel emits current pulses. The indicator lights green if the current is within the specified limits and red if outside the specified limits (for example, when the electrode chain is broken) (32). Autonomous control of the stimulator is carried out from the control and the indicating units located on the device. The channel number is selected by the button for setting the operation of each stimulation channel (33), the stimulation channel number is displayed on the panel (39). The channel triggering mode is selected by pressing the triggering button, iterating through the alphabetic mode codes, displayed on the panel (39). Not all triggering modes implemented by the instrument are available when the control is autonomous. It is possible to choose any of three pulse shapes and one of two triggering modes: continuous or one-time with the triggering button 4. The mode cipher consists of two symbols, the first one encodes the type of start, the second one is the pulse shape. Continuous start is encoded with the "C" symbol, a single one is "1". The unmodulated pulse shape is encoded by the symbol "N", the modulated monopolar pulse is represented by the symbol "M", the modulated bipolar pulse is encoded with the "B" symbol. The pulse frequency, duration of a single pulse, the amplitude of the current on the selected stimulation channel are set by buttons (35, 36, 37, respectively), the set values are displayed on the panel (39). The resistance value under the electrode is also displayed on the panel. There is a socket for connecting to the 220V network for charging batteries built into the stimulator (40) and a button for turning on the battery charge (41).

The computer is configured to set the current, the stimulation frequency, the pulse shape, the pulse duration and the channel start mode independently for each channel. The computer is configured to start each channel separately. It is possible to set the start of the channel depending on the triggering mode of another stimulation channel of the stimulator ("single-time from channel" and "continuous from channel" modes), choosing the delay time and the duration of the series by controlling from the computer, in contrast to the control from the panel of the electrostimulator using the director's console and the display unit. One more difference of management of a stimulator via the computer—the measured current is indexed near the set current for each channel.

FIG. 9-11 Tables 1A-1B shows the ratio between the set and the measured currents on one of the channels of the stimulator. The difference between the set and measured currents is usually less than or equal to 2 mA.

Researches were conducted on experimental base of the Velikiye Luki State Academy of Physical Culture and Sport. 7 physically healthy volunteers have been involved to researches.

The active electrodes were attached by epicutaneously along the central line of the spine between the spinous processes of the C4-C5, Th11-Th12 vertebrae, in the coccyx (Co vertebra), above the right and left roots of the spinal cord in the area of the Th11 vertebra. Round electrodes with a diameter of 2.5 cm with an adhesive layer (Lead-Lok, Sandpoint, USA) were used as cathodes. Each electrode was connected to the channel of a stimulator. A pair of rectangular electrodes measuring 5×10 cm2 with an adhesive layer (Ambu, Ballerup, FRG) were used as anodes.

The anodes were attached by epicutaneously in the abdominal area, above the iliac bones on the right and left sides. Anodes were connected to each other and served as a common "ground" for cathodes.

Voluntary and induced walking movements were performed on the experimental complex described by V. S. Gurfinkel et al. [Gurfinkel V S, Levik Yu. S., Kazennikov OV, Selionov V A, "Is there a generator of walking movements in humans?" Human Physiology, vol. 24, No. 3, p. 42-50, 1998]. The body weight support function is removed when the legs are horizontally suspended, allowing independent movements of both legs, since the subject lies on the side, and the right and left legs are in independent suspensions.

Figure 1:
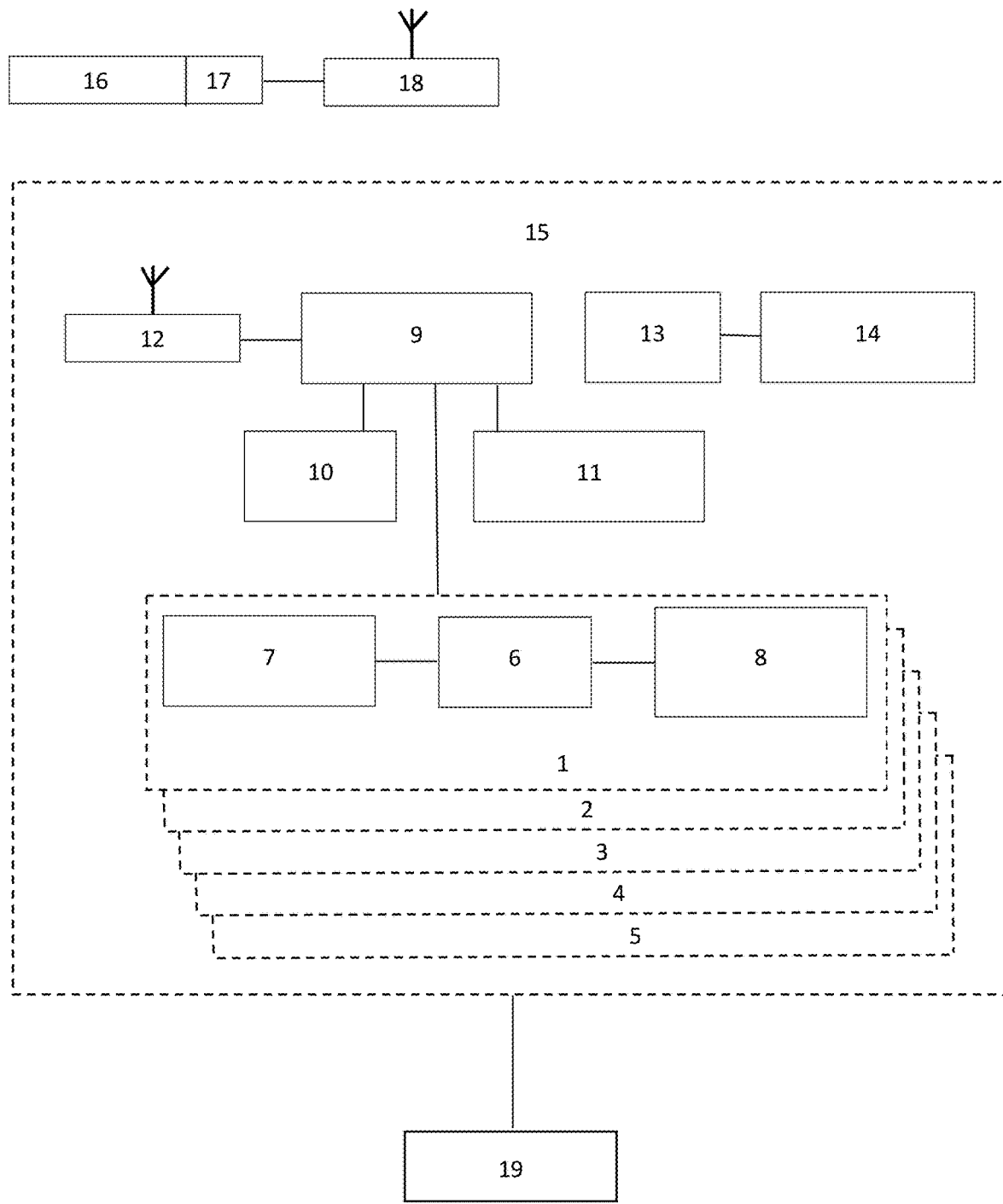
FIG. 1 depicts the block diagram of the stimulator.

In our researches subjects lay on the left side, the right (upper) leg was supported directly in a shin, and the left (lower) leg was placed on the rotating tire attached to horizontally focused board (1155×200 mm, 3 kg) withheld by the ropes fixed to a hook in a ceiling (FIG. 1). The instruction ordered to subjects not to interfere and not to help the movements caused by stimulation.

Electromyograms of 10 muscles of both legs were recorded by bipolar surface electrodes. EMG signals were collected using a telemetric 16-channel analog-to-digital converter (ADC) system (ME 6000 MegaWin, Finland). Leg movements in the knee joints were recorded using goniometers, also included in the ME 6000 MegaWin. The stimulation marks were given on 3 channels of this ADC system from 3 channels of the stimulator, the 1st, 3rd and 4th channels of the stimulator. The choice was due to the fact that the 1st and 2nd channels stimulator were used for paired stimulation of the roots of the spinal cord, the rhythm of the activity of the 1st channel determined the rhythm of the activity of the 2nd channel, information about this connection is stored in the study protocol and reproduced after the study. The 3rd channel of the stimulator was used to stimulate the spinal cord at the level of Th11-Th12 vertebrae. Channel 4 of the stimulator was used to stimulate the spinal cord at Co region. Channel 5 of the stimulator was used for stimulation at C5 level, it was not possible to record the sync signal from this channel on the ADC system, since the last, 16th channel of the ADC system is used for the service mark of the video system (Qualisys, Sweden), which was used to record the kinematic characteristics of the leg movements (data not shown).

FIG. 6 shows motor responses to Co stimulation by single monopolar unmodulated pulses of 1 ms duration. Stimulation current in mA, each intensity was repeated three times: 1, 10 (the subject felt the impact), 20, 30, 40 (the subject felt the impact, reacted "not painfully"), 50 (the subject felt the impact, reacted "not painfully", the observers saw the motor response of the leg muscles). The pulse marks are presented on the 15th recording channel (FIG. 6, Pos. 15). Durations of marks are made more than durations of pulses in order that the ADC has done not pass pulses with the used discrimination frequency 2 kHz. The irritation artifacts are visible on the EMG of the thigh muscles, starting at 1 mA (FIG. 6, Pos. 3-8), the reflex motor response is visible in the thigh muscles starting at 10 mA, the shin muscles (FIG. 6, Positions 1, 2, 9, 10) correspond with a current strength of 30 mA and more.

Thus, the stimulator can be used for transcutaneous stimulation of the spinal cord in order to record reflex responses of muscles.

FIG. 7 shows motor responses to stimulation with continuous monopolar modulated pulses of 1 ms duration, stimulation frequency 5 Hz, modulation frequency 10 kHz, stimulation current gradually increased from 1 to 45 mA. The duration of the mark on the 15th recording channel (FIG. 7, Pos. 15) corresponds to the duration of the stimulation. All notations are the same as in FIG. 6. There is a marked increase in the muscle response with an increase in the stimulation current on the records of the electromyographic signal (FIG. 7, Pos. 1-10). The motor response, the movements of both legs begins at approximately the intensity of the stimulation current of 30-40 mA. This was visible during the stimulation session, recorded in the protocol. The original record shows activity on the channels of goniometers (FIG. 7, Pos. 11, 12): increase of amplitude of bending in knee joints of both legs at increase in current of stimulation is visible. The flexures are unidirectional, with a small delay, it looked like a synchronized movement of two legs forward and backward, it was fixed on the video recording and when registered the kinematics of the movements (not shown here). After the end of stimulation on 107 s of recording (FIG. 7, Pos. 15), the continuing damped movements of both legs are visible, the burst electromyographic activity in the muscles of the thighs is visible (FIG. 7, Pos. 4, 6).

Thus, the stimulator can be used for transcutaneous stimulation of the spinal cord to cause involuntary movements. In this example, synchronous unidirectional movements of both legs were initiated.

FIG. 8 presents the original recording of the motor responses caused by transcutaneous stimulation of the spinal cord at two levels of the spinal cord by four stimulation channels: the electrodes were attached along the midline of the spine between the vertebrae Th11-Th12 (the 3rd channel of the stimulator, Pos. 14 in FIG. 8), above the vertebrae Co (4th channel of the stimulator, Pos. 15 in FIG. 8), over the roots of the spinal cord to the right and left of the vertebra Th11 (1st and 2nd stimulator channels). The 1st and 2nd channels of the stimulator were run antiphase, zero current flowed through the 1st channel to change the duty cycle and use only the right leg (1 second of stimulation on the 2nd channel, then 3 seconds of delay, the 1st channel corresponds to Pos. 13 in FIG. 8). The mode of bipolar modulated stimulation with a frequency of 30 Hz and a modulation frequency of 10 kHz for all channels was used. A current of 15 mA for 2-4 channels. A small current intensity selected, 2 times less than the one that caused involuntary movements of the legs in this subject. Noticeably tonic tension of the thigh muscles during the first three seconds of stimulation, when there is stimulation of the spinal cord at the region of Th11-Th12 and Co, current insufficient to cause movement (FIG. 8, Pos. 4-8), no leg movements. At the fourth second, the stimulation begins on the second channel of stimulation, which stimulates the spinal cord root on the right, at the level of Th11 vertebra. This causes step-like movements of the legs, first of all, the right leg reacts (FIG. 8, Pos. 11). Rhythmic step-like movements of the right leg develop 20 seconds after the start of stimulation in response to stimulation of the right spinal root (FIG. 8, Pos. 11), while the left leg performs low-amplitude nonrhythmic movements (FIG. 8, Pos. 12). Rhythmic movements of the right leg of the maximum amplitude are established 30 seconds after the start of the stimulation, there are episodes when the left leg makes step-like movements in antiphase with the right leg. Movements persist for 5 seconds after the end of stimulation.

Thus, the stimulator can be used to induce involuntary movements of the legs and to control these movements. In this example, first step-like movements were initiated with the right leg, then—step-like movements with two legs.

The foregoing description explains and in no way limits the present invention. Although the present invention has been described with reference to exemplary variant implementation, it should be understood that the explanations used in this document are illustrative and not limiting. Changes can be made within the competence of the attached invention claims. Although the present invention has been described herein with reference to specific implementation, it is not limited to the particulars disclosed in this document; rather, extends to all functionally equivalent structures, methods and uses are within the scope of the attached invention claims.

The invention claimed is:

1. A device for non-invasive stimulation of the spinal cord of a patient comprising
   an electrostimulator located in close proximity to the patient, the electrostimulator comprising five stimulation channels and an electrode system,
   wherein each of said five stimulation channels of the electrostimulator is connected to electrodes of the electrode system via wires, the electrodes being attached epicutaneously paraspine in a neck, thoracic, lumbar region or in a coccyx to stimulate the spinal cord and/or paravertebral in a projection of roots of the spinal cord to stimulate the roots of the spinal cord at least on one region of the spinal cord,
   wherein each of said stimulation channels includes a series-connected voltage converter, a current generator and an output signal shaper; and
   wherein each of said stimulation channels is configured to be able to generate at least one pulse selected from the group consisting of:
   rectangular single monopolar pulse for muscle activation,
   rectangular rhythmic monopolar pulses,
   rectangular rhythmic modulated monopolar pulses,
   rectangular rhythmic modulated bipolar pulses to trigger a locomotor response or trigger a tonic response in muscles, and
   combinations thereof
   with a stimulation frequency in the range of 1-99 Hz, with a current amplitude from 1 mA to 300 mA and with a modulation frequency from 4 kHz to 10 kHz;
   wherein inputs of each of said stimulation channels are connected to a microcontroller, connected to an indication unit, a control unit and a radio module;
   wherein said microcontroller is configured
   to trigger at least one of each said stimulation channels;
   to select a triggering mode independently for each of said stimulation channels; and
   to control each of the stimulation channels with parameters of the generated pulses, the parameters selected from the following:
   type of the pulses;
   the stimulation frequency, which may change in steps of 1 Hz or higher;
   the modulation frequency, which may change in steps of 1 kHz or higher;
   the current amplitude, which may change in steps of 1 mA or higher; and
   the pulse duration, which may change in steps of 0.1 ms or higher.

2. The electrostimulator of claim 1, wherein the microcontroller is configured to select the triggering mode between a single-time mode with a passive phase of depolarization and a continuous mode with active type of a phase of depolarization.

3. The electrostimulator of claim 1, wherein it is synchronized with external devices that have sync input, for example, with devices for registration of the caused motive answer as goniometers.

4. The electrostimulator of claim 1, wherein it is further connected to a computer.

5. The electrostimulator of claim 4, wherein triggering of at least one of each said stimulation channels, selection of the triggering mode independently for each of said stimulation channels, and control of each of said stimulation channels by parameters of the generated pulses are carried out by means of the computer.

6. The electrostimulator of claim 4, wherein triggering of at least one of each said stimulation channels, selection of the triggering mode independently for each of said stimulation channels, and control of each of said stimulation channels by the parameters of the rhythmic pulses are carried out by means of the computer, the control unit and the indication unit.

7. The electrostimulator of claim 4, wherein triggering of at least one of each said stimulation channel, selection of the triggering mode independently for each of said stimulation channels, and control of each of said stimulation channels by the parameters of the rhythmic pulses are carried out by means of the control unit and the indication unit.

* * * * *